United States Patent
Dawrant

(10) Patent No.: US 8,430,848 B1
(45) Date of Patent: Apr. 30, 2013

(54) RESERVOIR AND ADMINISTRATION DEVICE WITH RATCHETING MECHANISM

(76) Inventor: Jonathan Dawrant, Calgary (CA)

( * ) Notice: Subject to any disclaimer, the term of this patent is extended or adjusted under 35 U.S.C. 154(b) by 182 days.

(21) Appl. No.: 12/855,817

(22) Filed: Aug. 13, 2010

(51) Int. Cl.
*A61M 37/00* (2006.01)

(52) U.S. Cl.
USPC ........................................................ 604/132

(58) Field of Classification Search ............... 417/477.2; 604/132–314, 453
See application file for complete search history.

(56) References Cited

U.S. PATENT DOCUMENTS

| | | | |
|---|---|---|---|
| 4,340,048 A | 7/1982 | Eckenhoff | |
| 4,505,702 A | 3/1985 | Peery et al. | |
| 4,552,561 A | 11/1985 | Eckenhoff et al. | |
| 4,619,652 A * | 10/1986 | Eckenhoff et al. | 604/415 |
| 4,753,651 A | 6/1988 | Eckenhoff | |
| 5,693,018 A | 12/1997 | Kriesel et al. | |
| 5,848,990 A | 12/1998 | Cirelli et al. | |
| 6,048,337 A | 4/2000 | Svedman | |
| 6,074,372 A | 6/2000 | Hansen | |
| 6,436,078 B1 | 8/2002 | Svedman | |
| 6,524,280 B2 | 2/2003 | Hansen et al. | |
| 6,582,404 B1 | 6/2003 | Klitgaard et al. | |
| 6,692,472 B2 | 2/2004 | Hansen et al. | |
| 6,702,779 B2 | 3/2004 | Connelly et al. | |
| 6,855,133 B2 | 2/2005 | Svedman | |
| 6,896,666 B2 | 5/2005 | Kochamba | |
| 7,104,972 B2 | 9/2006 | Moller et al. | |
| 7,678,079 B2 | 3/2010 | Shermer et al. | |
| 2008/0051727 A1 | 2/2008 | Moberg et al. | |
| 2008/0215006 A1 | 9/2008 | Thorkild | |
| 2008/0215029 A1 * | 9/2008 | Rake et al. | 604/408 |
| 2009/0259182 A1 | 10/2009 | Cross et al. | |

* cited by examiner

*Primary Examiner* — Kevin C Sirmons
*Assistant Examiner* — Bradley Osinski
(74) *Attorney, Agent, or Firm* — David A. Guerra

(57) ABSTRACT

A fluid reservoir and administration device for delivering a dosage of a medicament to a patient. The device has a base unit attachable to the skin, a reservoir unit attachable to the base unit, and a cap unit attachable to the reservoir unit. The base unit has a latching member, and a needle. The reservoir unit has a fluid filled cavity, a ratcheting element, a threaded member, and a plunger for forcing the fluid through the needle. The cap unit has ratcheting teeth engagable with the ratcheting member, and a threaded post engagable with the threaded member of the reservoir unit. When the cap unit is rotated, the threaded post is advanced toward the plunger which forces a metered dosage of the fluid through the needle and to the patient. The ratcheting member allows the cap unit to rotate in a single direction, thereby preventing a vacuum in the cavity.

19 Claims, 5 Drawing Sheets

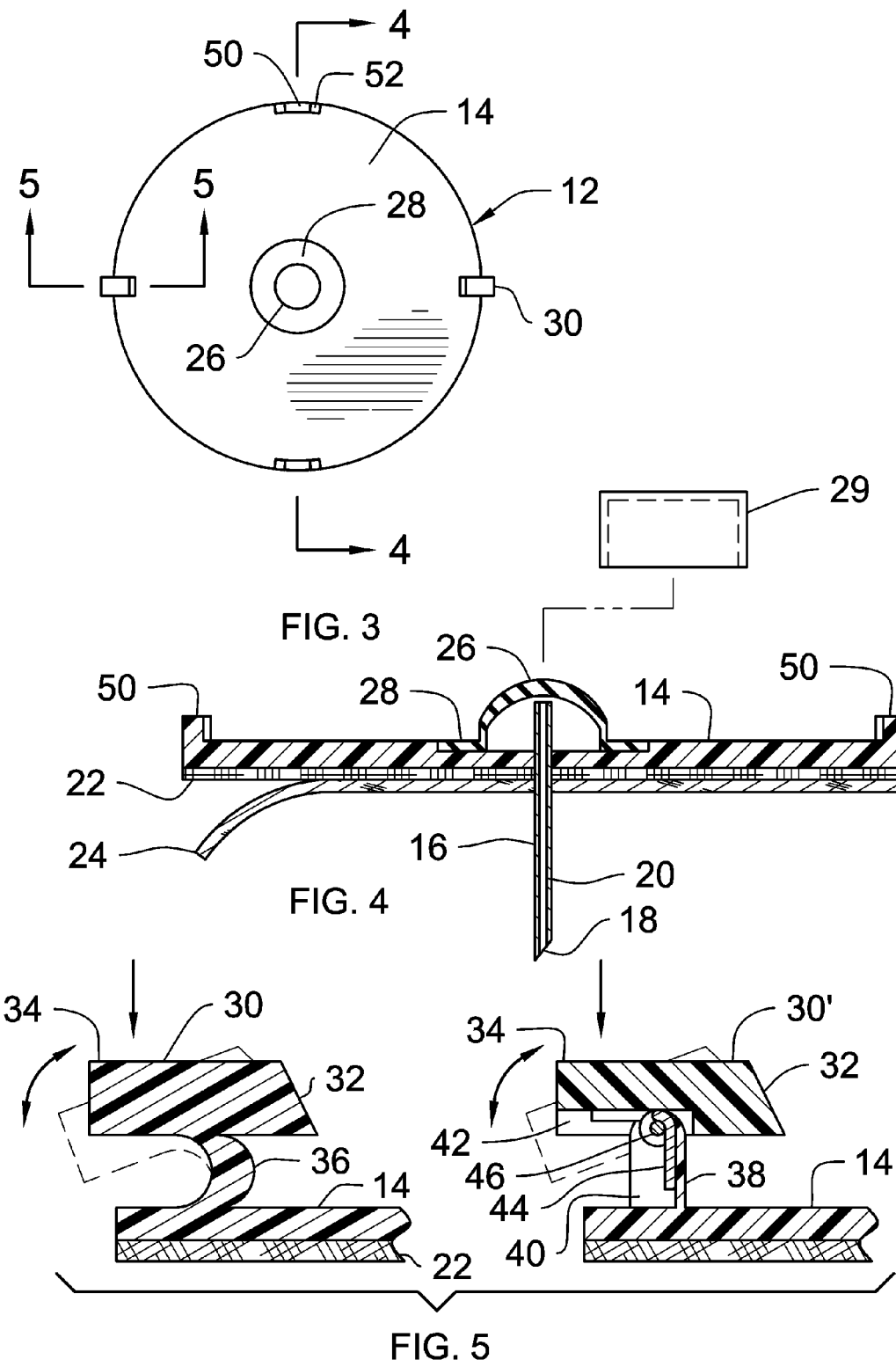

RESERVOIR AND ADMINISTRATION DEVICE WITH RATCHETING MECHANISM

CROSS-REFERENCE TO RELATED APPLICATION

Not applicable

FEDERALLY SPONSORED RESEARCH

Not applicable

SEQUENCE LISTING OR PROGRAM

Not applicable

BACKGROUND OF THE INVENTION

1. Field of the Invention

The present invention relates generally to a wearable insulin delivering button. In particular, it is concerned with a wearable, disposable insulin reservoir and administration device for use in connection with delivering a dosage of insulin or medicament to a patient discreetly and efficiently.

2. Description of the Prior Art

Wearable, disposable insulin reservoir and administration devices are desirable for providing a user or patient an efficient and discreet device for delivering a dose of insulin or other medicament, while allowing for the quick replacement of the device when depleted.

Diabetes is a chronic disease that is characterized by the body's inability to control glucose levels. Left untreated, it causes damage to the circulatory and nervous systems and results in organ failures, amputations, neuropathy, blindness and eventually death. It has been definitively shown that the cost of the complications related to diabetes significantly exceeds the cost of therapy.

Tight control over the delivery of insulin in both type I diabetes (usually juvenile onset) and type II diabetes (usually late adult onset), has been shown to improve the quality of life as well as the general health of these patients. Proper control of blood glucose levels through programmed insulin injection or infusion allows a high quality of life and longer life expectancy.

Insulin delivery has been dominated by subcutaneous injections of both long acting insulin to cover the basal needs of the patient and by short acting insulin to compensate for meals and snacks. There are two standard systems of daily insulin therap.

The first being syringes and insulin pens. These devices are simple to use and are relatively low in cost, but they require a needle stick at each injection, typically multiple times per day. These device must be carried by the user, so thereby putting the burden on the user to carry enough devices to sustain there activities away from home or medical facilities.

The second and most recent development is infusion pump therapy, which entails the purchase of an expensive pump that lasts for about three years. External insulin infusion pumps have allowed the continuous infusion of fast acting insulin for the maintenance of the basal needs as well as the compensatory doses (boluses) for meals and snacks. However, they suffer the drawbacks of being large in size, cost, and high complexity. For example, these pumps are electronically controlled and must be programmed to supply the desired amounts of basal and bolus insulin. This prevents many patients from accepting this technology over the standard subcutaneous injections. Additionally, the initial cost of the pump is a high barrier for many patients.

Several attempts have been made to provide ambulatory or "wearable" drug infusion devices. This type of wearable device can provide many of the advantages of an infusion pump without its disadvantages. However, many of these known devices cannot provide precise control over the dosage delivery of the drug at a low delivery cost, and are thus not practical with dose-critical drugs such as insulin.

While the above-described devices fulfill their respective, particular objectives and requirements, the aforementioned patents do not describe a wearable, disposable insulin reservoir and administration device that allows delivering a dosage of insulin or medicament to a user discreetly and efficiently.

Therefore, a need exists for a new and improved wearable, disposable insulin reservoir and administration device that can be used for delivering a dosage of insulin or medicament to a user discreetly and efficiently. In this regard, the present invention substantially fulfills this need. In this respect, the wearable, disposable insulin reservoir and administration device according to the present invention substantially departs from the conventional concepts and designs of the prior art, and in doing so provides an apparatus primarily developed for the purpose of delivering a dosage of insulin or medicament to a user discreetly and efficiently.

SUMMARY OF THE INVENTION

In view of the foregoing disadvantages inherent in the known types of wearable medicine buttons now present in the prior art, the present invention provides an improved wearable, disposable insulin reservoir and administration device, and overcomes the above-mentioned disadvantages and drawbacks of the prior art. As such, the general purpose of the present invention, which will be described subsequently in greater detail, is to provide a new and improved wearable, disposable insulin reservoir and administration device and method which has all the advantages of the prior art mentioned heretofore and many novel features that result in a wearable, disposable insulin reservoir and administration device which is not anticipated, rendered obvious, suggested, or even implied by the prior art, either alone or in any combination thereof.

To attain this, the present invention essentially comprises a fluid reservoir and administration device for delivering a dosage of a medicament to a patient. The device broadly has a base unit, a reservoir unit attachable to the base unit, and a cap unit attachable to the reservoir unit. The base unit has a main support, at least one latching member, and at least one needle. The reservoir unit has a housing defining a cavity therein filled with a fluid, at least one ratcheting element located on an exterior of the housing, a threaded member, and a plunger moveable received in said cavity. The housing further has a base configured to be releasably secured to the main support of the base unit by the latching member of the base unit. The cap unit has a side wall, a top wall, a defined open bottom configured to receive the reservoir unit therein, a plurality of ratcheting teeth extending interiorly from the side wall, and a threaded post extending interiorly from the top wall toward the open bottom. The ratcheting teeth are configured to engage with the ratcheting member of the reservoir unit respectively. The threaded post is configured to threadably engage with the threaded member of the reservoir unit. The threaded post has a distal end configured to be contact with and move the plunger of the reservoir unit when the cap unit is rotated. The proximal end of the needle is in fluid communication with the fluid in the cavity of the reservoir unit when the reservoir unit is fitted to the base unit.

The main support of the base unit further has an adhesive layer, at least one ridge located adjacent a periphery of the main support, and a sheath fixed to the main support and positioned so as to cover a proximal end of the needle. The ridge is configured to guide and retain the base of the reservoir unit in a position on the base unit.

There has thus been outlined, rather broadly, the more important features of the invention in order that the detailed description thereof that follows may be better understood and in order that the present contribution to the art may be better appreciated.

The invention may also include multiple fingers extending angularly away from the top wall of the reservoir unit and toward each other. With each of the fingers having a distal end which terminate before contacted the distal ends of the remaining fingers and which face each other. The distal ends include threads so as to define a threaded opening between the distal ends of the fingers.

Even further, the invention may also include a seal in the base of the reservoir unit that is configured to be perforated by the proximal end of the needle when the reservoir unit is fitted to the base unit.

There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved wearable, disposable insulin reservoir and administration device that has all of the advantages of the prior art wearable medicine buttons and none of the disadvantages.

It is another object of the present invention to provide a new and improved wearable, disposable insulin reservoir and administration device that may be easily and efficiently manufactured and marketed.

An even further object of the present invention is to provide a new and improved wearable, disposable insulin reservoir and administration device that has a low cost of manufacture with regard to both materials and labor, and which accordingly is then susceptible of low prices of sale to the consuming public, thereby making such wearable, disposable insulin reservoir and administration device economically available to the buying public.

Still another object of the present invention is to provide a new wearable, disposable insulin reservoir and administration device that provides in the apparatuses and methods of the prior art some of the advantages thereof, while simultaneously overcoming some of the disadvantages normally associated therewith.

Even still another object of the present invention is to provide a wearable, disposable insulin reservoir and administration device for delivering a dosage of insulin or medicament to a user discreetly and efficiently. This allows for the administering of a metered dose of insulin to the patient using a disposable, cost effective and easy to use device that the patient can apply and administer as needed.

Most patients with diabetes use more than one type of insulin during a day. The ability of the reservoir unit to be removed form the base unit allows a patient to switch between insulin's by replacing and switching between different reservoir units containing different insulin's. The net effect is that for the approximate three day duration of the base unit being in-situ the patient is wearing only one base unit and has only been required to undergo one uncomfortable insertion event. Note that this is possible because most insulin's are compatible with each other and can be mixed in one syringe or injected into one depot location under skin. Therefore there is not concern for cross-contamination between insulin's in the base unit.

The removability of the reservoir unit from the base unit is particularly useful for young patients with diabetes from whom multiple injections are painful but who are too immature to trust unsupervised with the reservoir unit attached. The parent would do one insertion event every three days then administer each insulin dose by briefly attaching, dialing the dose (rotating the cap unit) and then removing the reservoir unit. In this manner, multiple daily doses can be administered with no injections. This routine would also benefit any adults with diabetes who also suffer needle phobia or cognitive impairments such that they should not be left alone with an attached insulin reservoir.

Historical insulin administration devices use 300 unit cartridges. Because frequent switching out of the reservoir unit is easily done with the present invention, as it offers the possibility of small volume (e.g. 100, 200 unit) reservoir units. Small volume reservoir units are correspondingly flat which enable the entire system to be worn very unobtrusively.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a top elevational view of the base unit of the wearable, disposable insulin reservoir and administration device of the present invention.

FIG. 4 is a cross-section view of the base unit of the wearable, disposable insulin reservoir and administration device of the present invention, taken along line 4-4 of FIG. 3.

FIG. 5 is an enlarged cross-sectional view of the latch of the base unit of the present invention.

The same reference numerals refer to the same parts throughout the various figures.

DESCRIPTION OF THE PREFERRED EMBODIMENT

Figure 1:
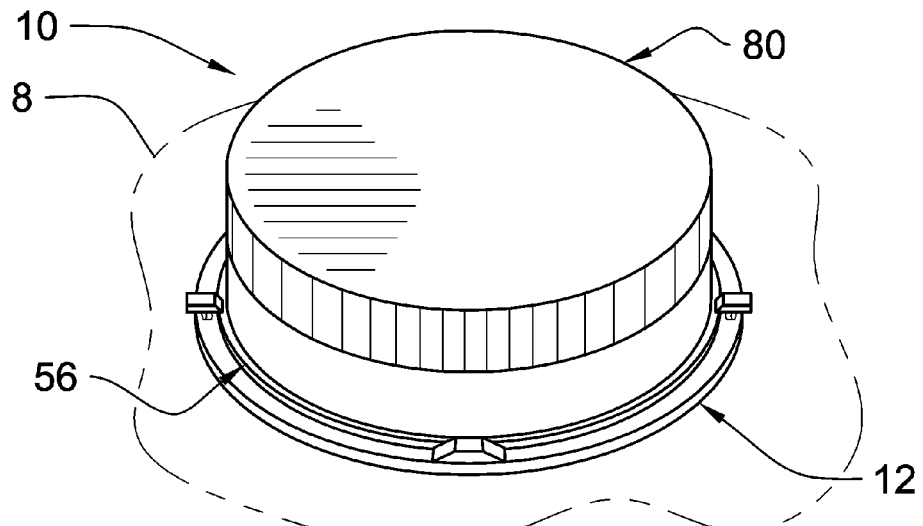
FIG. 1 is a perspective view of the preferred embodiment of the wearable, disposable insulin reservoir and administration device constructed in accordance with the principles of the present invention, with the phantom lines depicting environmental structure and forming no part of the claimed invention.

Referring now to the drawings, and particularly to FIGS. 1-12, a preferred embodiment of the wearable, disposable insulin reservoir and administration device of the present invention is shown and generally designated by the reference numeral 10.

Figure 2:
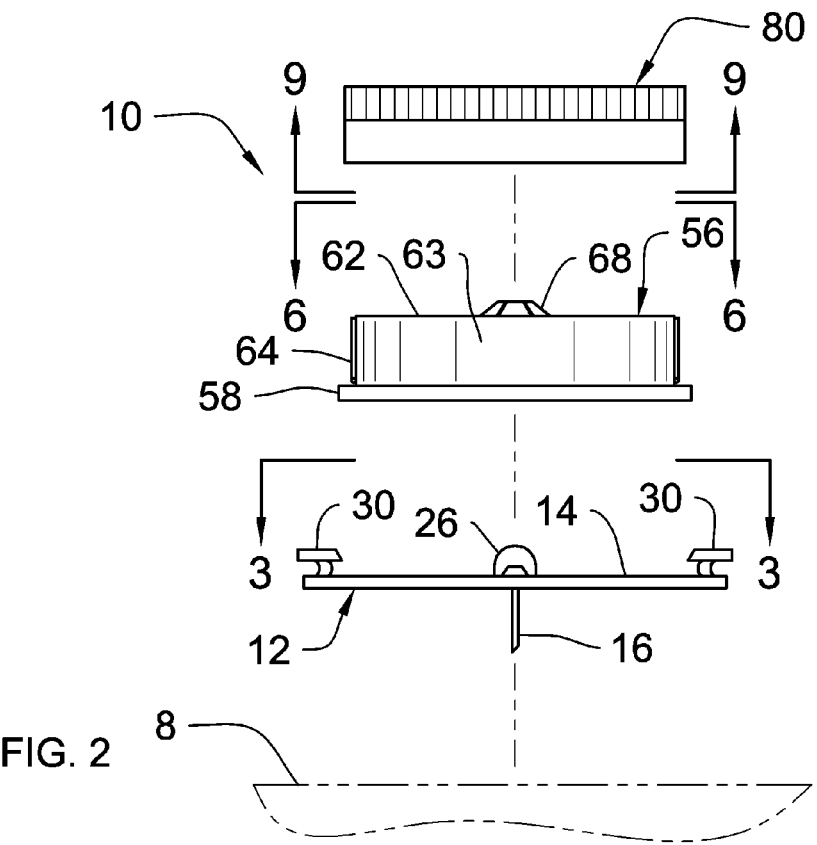
FIG. 2 is an exploded perspective view of the wearable, disposable insulin reservoir and administration device of the present invention.

In FIGS. 1 and 2, a new and improved wearable, disposable insulin reservoir and administration device 10 of the present invention for delivering a dosage of insulin or medicament to a user discreetly and efficiently is illustrated and will be described. More particularly, the wearable, disposable insulin reservoir and administration device 10 has a base unit 12 removably attached to the skin 8 of a user or patient, a reservoir unit 56 removably attached to the base unit 12, and a cap unit 80 threadably engaged with and removably attached to the reservoir unit 56.

The base unit 12 has a main support 14 including one or more latches 30, one or more guide ridges 50, and a flexible sheath 26, as illustrated in FIG. 3. The main support 14 has a, but not limited to, generally circular configuration with the latches 30, and ridges 50 radially located along a periphery thereof. The main support 14, latches 30, and ridges 50 are made of, but not limited to, plastics, polyethylene, polystyrene, polyvinyl chloride and polytetrafluoroethylene (PTFE). It can be appreciated that any suitable material that is human safe or medical grade can be used for the main support, latches, ridges and sheath.

As best illustrated in FIG. 4, the base unit 14 is firmly secured to the skin 8 of the patient by way of an adhesive layer 22 that is temporally protected by a removable peel-away cover 24. The adhesive layer 22 is located on a side of the main support 14 opposite the sheath 26, latches 30, and ridges 50, and is able to securely and removably attach to the patient's skin 8. A needle 16 projects through at least the base unit 14 and the adhesive layer 22 so as to extend out past both sides of the main support 14. It can be appreciated that the needle 16 can extend out past the side containing the adhesive layer 22 a distance sufficient enough to penetrate in or through the skin 8 and/or into the fatty layer beneath the skin. The needle 16 can be of any gauge required by the patient, and different base units 12 can be used containing different needle 16 lengths and gauges. The needle 16 has an angled distal end 18 in communication with a lumen 20 defined through the needle 16. The needle 16 is made of, but not limited to, any medical grade or human safe metals, plastics, and alloys.

The sheath 26 has a generally dome-like configuration including a flange 28 extending outwardly from a bottom of the dome sheath 26. The flange 28 is attached to and received in a recess centrally defined in the main support 14 so that the dome sheath 26 covers a proximal end of the needle 16 opposite its distal end 18. The sheath 26 is flexible and preferably made of, but not limited to, rubber, so that the needle 16 can penetrate through the dome sheath 26 when the dome sheath is pressed down on the proximal end of the needle 16. The sheath 26 functions as a cover and a basic occlusion device for the needle 16, and has a thicker upper occluding portion in comparison to its side walls and the flange 28 of the sheath 26. In a resting position, as best illustrated in FIG. 4, the proximal end of the needle 16 is inside the sheath 26 which provides enough resistance to any insulin or physiological fluid trying to move back up the lumen 20 of the needle 16. When the sheath 26 is depressed, the proximal end of the needle 16 perforates the upper occluding portion to expose the proximal end. The sheath 26 and the proximal end of the needle 16 can be covered by a releasable sheath cap 29, thereby protecting the sheath 26 from accidental depression or damage, or from injuring the user while transporting, applying or disposing the base unit 12. Additionally, the needle 16 can include a removably protective sleeve (not shown) or may be covered by the peel-away cover 24.

The latch 30, as best illustrated in FIG. 5, has an angled inner surface 32, a substantially top planar surface 34, and a biasing element 36 that connects the latch 30 to the main support 14. The angled inner surface 32 has a generally downward and inwardly angled surface toward the main support 14 so as to allow the reservoir unit 56 to be securely latched between the latch 30 and the main support 14. The biasing element 36 provides a securing or snapping force to the reservoir unit 56 by way of biasing the latch 30 in a pivoting motion toward the base 58 of the reservoir unit 56. The reservoir unit 56 is released from the latch 30 by applying a force to the top surface 34 against the force of the biasing element 36 which pivots the latch 30 away from the base 58 of the reservoir unit 56 thereby allowing the reservoir unit to be removed therefrom. The latch 30, biasing element 36 and the main support 14 can be integrally formed in a single piece, with the biasing element 36 being a flexible post between the latch 30 and the main support 14. The flexible post biasing element 36 can have, but not limited to, a curve, arcuate or straight configuration. It can be appreciated that the base unit 12 can include multiple latches 30 radially located opposite each other near the peripheral edges of main support 14.

An alternate embodiment latch 30', as best illustrated in FIG. 5, has an angled inner surface 32, a substantially top planar surface 34, and a biasing element 44 that provides a biased pivoting force to the latch 30' toward the main support 14. The biasing element 44 is a spring, such as but not limited to, a coil spring, a leaf spring, or a torsion spring. The angled inner surface 32 has a generally downward and inwardly angled surface toward the main support 14 so as to allow the reservoir unit 56 to be securely latched between the latch 30' and the main support 14. The main support 14 includes an upwardly extending support 38 defining a notch 40 for receiving a portion of the spring 44, and the latch 30' defines a notch 42 for receiving an opposite portion of the spring 44. A shaft or pin 46 extends through the support 38 and its notch 40, and the latch 30' and its notch 42, thereby securing the latch 30' to the support 38. The spring 44 may have a coil section configured to receive the pin 46 therethrough. The spring 44 provides a securing or snapping force to the reservoir unit 56 by way of biasing the latch 30' in a pivoting motion toward the reservoir unit 56. The reservoir unit 56 is released from the latch 30' by applying a force to the top surface 34 against the force of the spring 44 which pivots the latch 30' away from the reservoir unit 56 thereby allowing the reservoir unit to be removed therefrom. It can be appreciated that the base unit 12 can include multiple latches 30' radially located opposite each other near the peripheral edges of main support 14.

The guide ridges 50 extend up from the peripheral edge of the main support 14 for assisting and guiding the placement of the reservoir unit 56 onto the main support 14. The guide ridges 50 each have angle edges 52 located at opposite ends thereof, and each have a curved configuration with an inner radius equal to or less than the radius of the main support 14. It can be appreciated that the base unit 12 can include multiple guide ridges 50 radially located opposite near the peripheral edges of main support 14.

Figure 6:
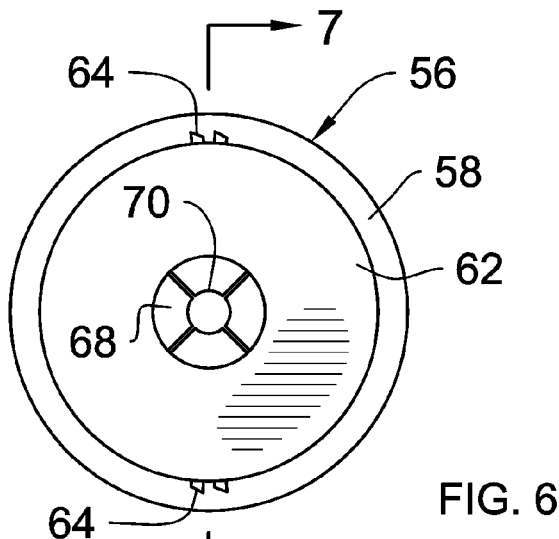
FIG. 6 is a top elevational view of the reservoir unit of the wearable, disposable insulin reservoir and administration device of the present invention.
Figure 7:
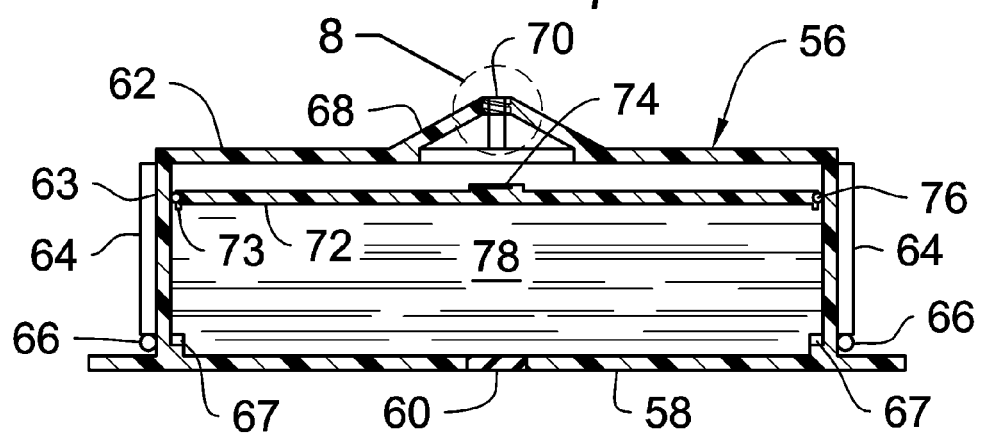
FIG. 7 is a cross-section view of the reservoir unit of the wearable, disposable insulin reservoir and administration device of the present invention, taken along line 7-7 of FIG. 6.

The reservoir unit 56, as best illustrated in FIGS. 6 and 7, has a base 58, a substantially cylindrical side wall 63 extending up from the base 58, a top wall 62 extending across the side wall 63, and fingers 68 angularly extending up from the top wall 62. The reservoir unit 58 includes a moveable plunger 72 located in an interior chamber formed by the base 58, side wall 63, and top wall 62. The chamber is prefilled with a fluid 78, such as but not limited to, insulin or medicament. The base 58, side wall 63, top wall 62, and plunger 72 are made of, but not limited to, a medical grade glass or plastic.

The base 58 has a generally cylindrical configuration with a diameter larger than the radius of angled inner surface 32 of the latch 30, 30', and less than the radius of the biasing element 36 of latch 30 or support 38 of the latch 30' respectively. The base 58 includes a rubber seal 60 centrally located through the base 58, and one or more notched ramps 67 extending up from the base 58 and formed integrally with the interior of the side wall 63. The notched ramps 67 feature opposing angled or ramp-like faces with a notch defined between the faces. The rubber seal 60 is adapted to be perforated by the proximal end of the needle 16 when the reservoir unit 56 is inserted onto and received by the base unit 12, thereby forcing the seal 60 against the sheath 26 and depressing the sheath to expose the proximal end of the needle 16. The rubber seal 60 does not allow insulin 78 to leak behind thereof, thereby providing a tight fluidic seal between the seal 60 and the needle 16.

The outer surface of the side wall 63 includes one or more ratcheting ledges 64 extending along the height of the side wall 63 parallel with the longitudinal axis of reservoir unit 56. A spherical element 66 is located adjacent an end of each ratcheting ledge 64 and adjacent the base 58, so that the spherical element 66 is located between the end of the ratcheting ledge 64 and an upper surface of the base 58, as best illustrated in FIG. 7. The ratcheting ledges 64 include an angled side and a planar side. The ratcheting ledges 64 consist of, but not limited to, a pair of two ledges 64 located on opposite sides of the side wall 63, with each ledge 64 having their ratcheting face in the same rotations direction, as best illustrated in FIG. 6. It can be appreciated that additional ledges 64 can be incorporated around the outer circumference of the side wall 63.

Figure 8:
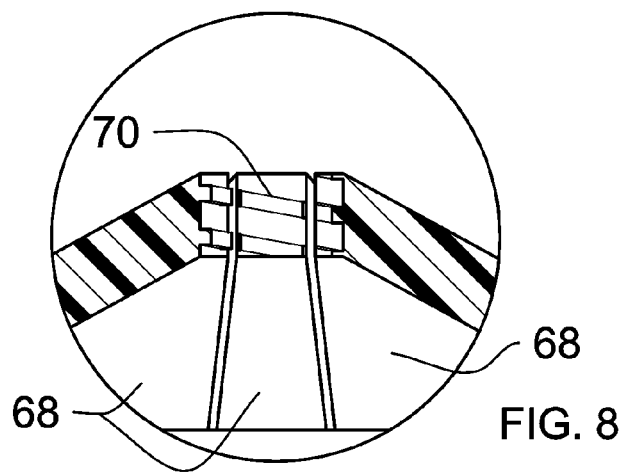
FIG. 8 is an enlarge cross-section view of a threaded top portion of the reservoir unit of the present invention.

FIG. 8 best illustrates the fingers 68 of the top wall 62 of the reservoir unit 56. The fingers 68 consisting of multiple angled members of semi-stiff plastic angularly extending up from the top wall 62. The fingers 68 each have a distal end 70 which terminates before contacting the distal ends of the remaining fingers so as to form an opening or bore inline with the longitudinal axis of the reservoir unit 56 and with the rubber seal 60 of the base 58. The distal ends 70 of each finger 68 are interiorly threaded, with the threads being substantially perpendicular to the longitudinal axis of the reservoir unit 56.

The plunger 72 includes one or more protrusions 73, and a recess 74 centrally located and inline with the longitudinal axis of the reservoir unit 56, the bore defined by the fingers 68, and the rubber seal 60 of the base 58. The protrusions 73 extend downward from a bottom of the peripheral edge of the plunger 72, and have a radius substantially equal to the radius of the notched ramp 67. The defined notch in the notched ramp 67 is configured to receive one protrusion 73 therein, and the ramp-like faces guide the protrusion 73 into the notch. An O-ring seal or gasket 76 is located along the periphery of the plunger 72 so as to make a fluidic seal between the plunger 72 and the interior of the side wall 63. The plunger 72 is moveable along the longitudinal axis of the reservoir unit 56 so as to force insulin 78 through the proximal end of the needle 16 exposed through the rubber seal 60 of the base 58 when the reservoir unit 56 is received in the base unit 12.

Figure 9:
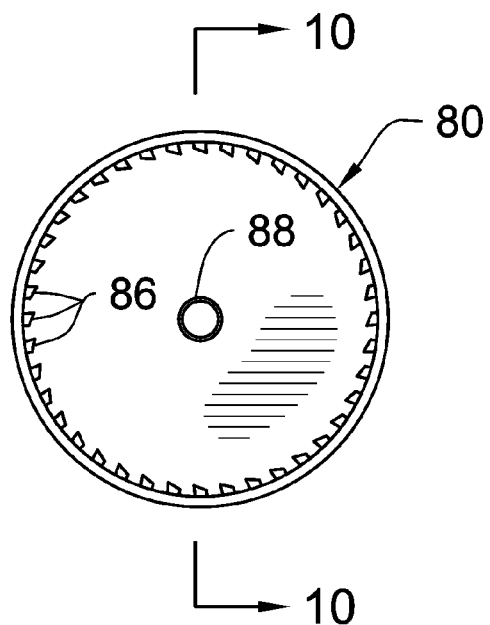
FIG. 9 is a bottom elevational view of the cap unit of the wearable, disposable insulin reservoir and administration device of the present invention.
Figure 10:
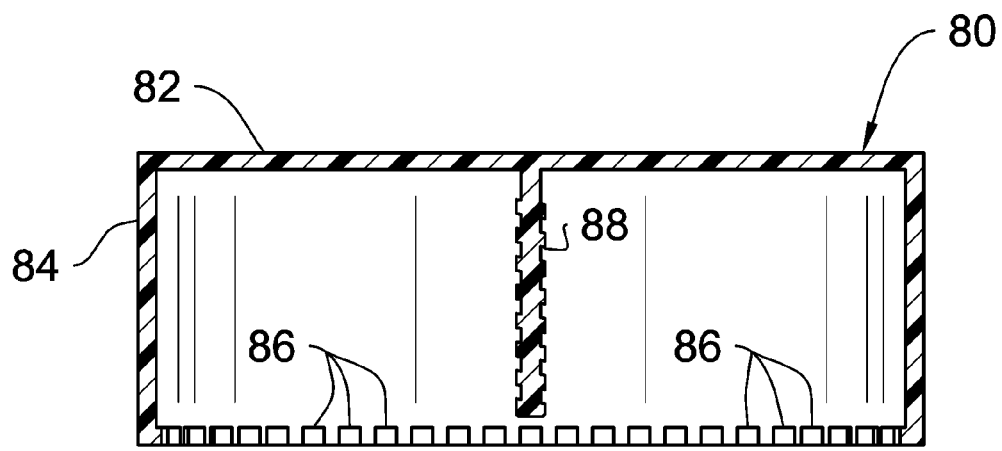
FIG. 10 is a cross-section view of the cap unit of the wearable, disposable insulin reservoir and administration device of the present invention, taken along line 10-10 of FIG. 9.

The cap unit 80, as best illustrated in FIGS. 9 and 10, has a generally cylindrical configuration including a top wall 82, a cylindrical side wall 84, multiple ratcheting teeth 86, and a threaded post 88. The top wall 82 extends across the side wall 84, so as to form an opened bottom cylinder defining an interior cavity. The side wall 84 may contain ridges, grooves or grips along a portion thereof for assisting the user in manipulating the cap unit 80. The cap unit 80 is made of, but not limited to, plastics, polyethylene, polystyrene, polyvinyl chloride, and PTFE. The side wall 84 of the cap unit 80 has a diameter larger than the diameter of the side wall 63 of the reservoir unit 56, and less than the radius of the latch 30, 30' of the base unit 12. The side wall 84 further has a height larger than the height of the reservoir unit 56.

The ratcheting teeth 86 are located along the interior circumference of a distal end of the side wall 84, and have a generally square configuration. When the cap unit 80 is rotated in one radial direction, the ratcheting teeth 86 are configured and sized to slide along the angled side of the ratcheting ledges 64. When the cap unit 80 is rotated in an opposite radial direction, the ratcheting teeth 86 engage or abut against the planar side of the ratcheting ledges 64 of the reservoir unit 56. Thus the cap unit 80 can only rotate in a single radial direction when the ratcheting teeth 86 are engaged with the ratcheting ledges 64, since the ratcheting face or angled side of the ledges 64 are angled in one direction, and the planar side prevents the cap unit 80 from rotating in the opposite direction. It can be appreciated that the ratcheting teeth 86 are able to freely rotate in either radial direction when they are adjacent the spherical elements 66 since the spherical elements 66 do not have a planar face or side to abut against the ratcheting teeth 86.

The post 88 extends into the cavity of the cap unit 80 centrally from the top wall 82, as best illustrated in FIG. 10, and has external threads that engage with the internally threaded distal ends 70 of the fingers 68 of the reservoir unit 56. The post 88 includes a non-threaded portion adjacent the top wall 82. The post 88 includes a distal end configured to be received in the recess 74 of the plunger 72 of the reservoir unit 56, thereby applying a force against the plunger 72 to move the plunger when the cap unit 80 is rotated. The non-threaded section of the post 88 has a size and location to allow the distal ends 70 of the fingers 68 to freely rotate in any radial direction when the ratcheting teeth 86 are adjacent the spherical members 66 of the reservoir unit 56.

Figure 11:
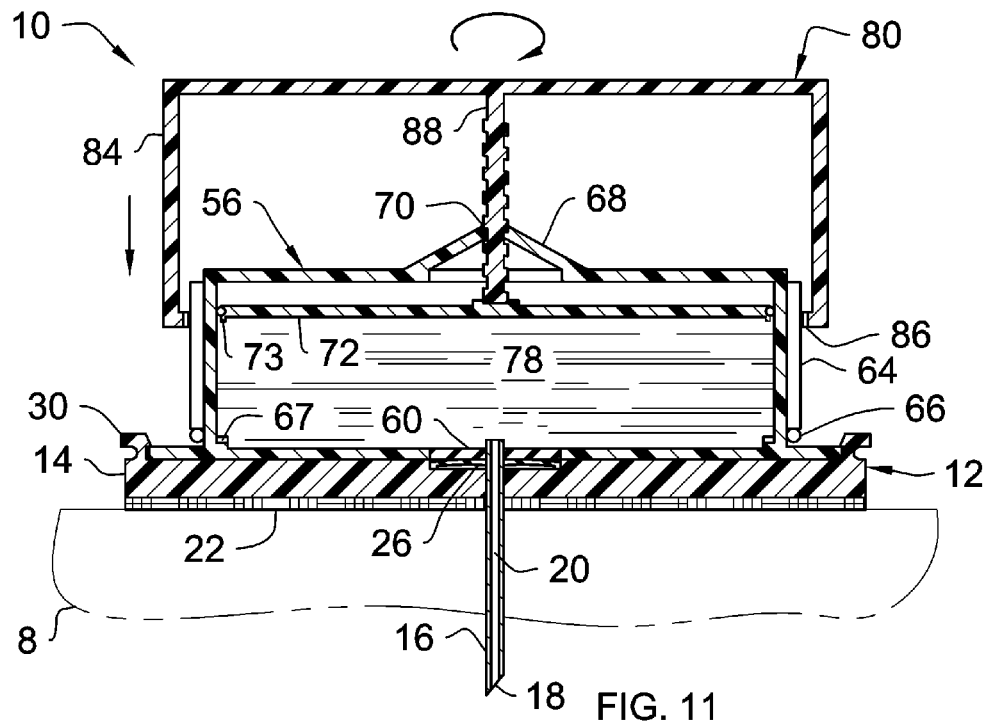
FIG. 11 is a cross-section view of an in use and assembled wearable, disposable insulin reservoir and administration device of the present invention.
Figure 12:
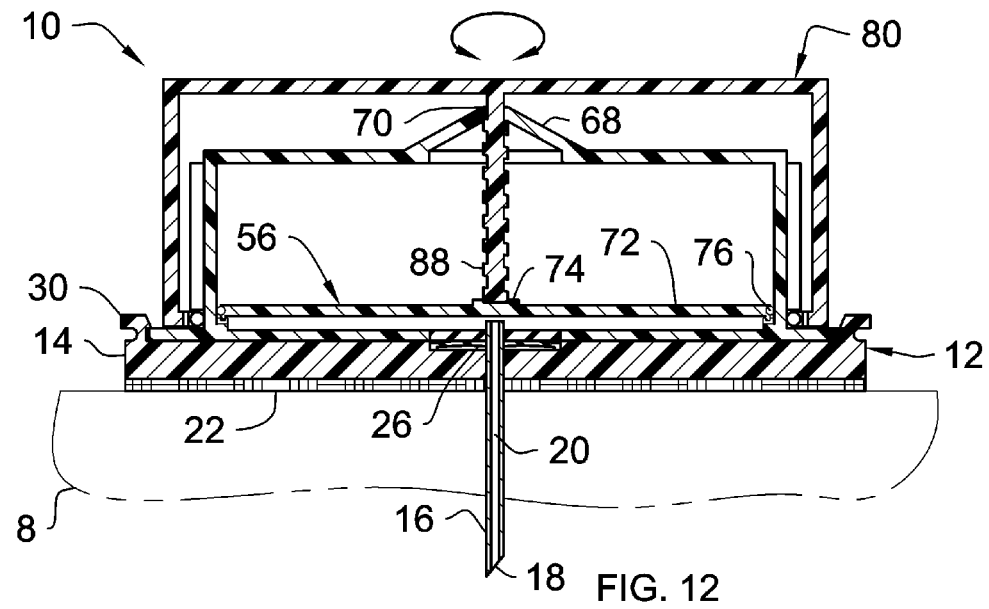
FIG. 12 is a cross-section view of a depleted wearable, disposable insulin reservoir and administration device of the present invention.

In use, as best illustrated in FIGS. 11 and 12, it can now be understood that the user would peal away the temporary cover 24 of the base unit 12 to expose the adhesive layer 22. The base unit 12 is then applied to the skin 8 of the user so that the angled distal end 18 of the needle 16 penetrates the skin 8. The adhesive layer 22 securely adheres the base unit 12 to the skin 8, so as not to allow accidental movement or removal of the base unit 12. The cap 29 is then removed to expose the sheath 26.

The reservoir unit 56 is then placed on the base unit 12 so that the base 58 of the reservoir unit 56 is received within guide ridges 50 and snapped and locked into place by the latch 30, 30'. The peripheral edge of the base 58 contacts the angled surface 32, and deflects the latch 30, 30' so as to allow the base 58 to be received in the space between the latch 30, 30' and the base 58. The biasing element 36, 44 of the latch 30, 30' provide a securing force toward the base 58 of the reservoir unit 56 thereby retaining the reservoir unit against a top surface of the main support 14 of the base unit 12, so that the rubber seal 60 depresses the sheath 26 down in the recess of the main support 14. Depressing the sheath 26 by the reservoir unit 56 exposes the proximal end of the needle 16 through the sheath 26 and the rubber seal 60. The proximal end of the needle 16 is now in fluid communication with the insulin 78 in the reservoir unit 56.

The cap unit 80 is then placed on the reservoir unit 56 and rotated so that the threaded post 88 is engaged with the threaded ends 70 of the fingers 68, and that the distal end of the post 88 is received in the recess 74 of the plunger 72 of the reservoir unit 56. It can be appreciated that the base unit 12, the reservoir unit 56, and the cap unit 80 can be assembled and primed prior to application on the patient.

It can further be appreciated that the cap unit 80 reduces cost by allowing the cap unit to be reused since it is not in direct contact with the insulin 78. However, should manufacturing economics be advantageous, the present invention could be simplified to having the cap unit 80 pre-attached to the reservoir unit 56 with no need for later removal, thereby combining the cap unit and the reservoir unit into a single preassemble unit.

The user can then rotate cap unit 80 in a single direction so that the ratcheting teeth 86 of the cap unit 80 engage with the ratcheting ledges 64 of the reservoir unit 56. Each turn of the cap unit 80 advances the plunger 72 toward the base unit 12 a predetermined distance, thereby forcing a predetermined amount or dose of insulin 78 through the needle 16 and to the patient. Since the ratcheting ledges 64 have a single angular ratcheting face, it can then be appreciated that the cap unit 80 can only be rotated in a single direction, thereby preventing the plunger 72 from being retreated back into the reservoir unit 56 and creating a suction force through the needle 16. Each turn of the cap unit 80 produces a click-like sound from the ratcheting teeth 86 and ledges 64, thereby giving the user an audible indication of rotation and administration of insulin.

It can be appreciated that the dosage amount dispensed through the needle 16 is related to the angle of the threads in the threaded distal end 70 of the fingers 68 and the threaded post 88. The greater the angle of the threads the greater the dosage amount per rotation of the cap unit 80. Different cap units 80 with varying thread angles can be used for varying dosages, thereby providing the patient the ability to alter dosing in relation to the patients diabetes type, age, glucose level, or any other factor relating to insulin dosage. Furthermore, the patient can perform multiple rotations of the cap unit 80 to provided multiple metered dosages of insulin 78.

The angled configuration of the fingers 68 prevents the unwanted and accidental advancement of the cap unit 80 by a pushing force against the cap unit 80 in the longitudinal direction, but allows for withdrawal of the cap unit 80 in an opposite direction.

When the user rotates the cap unit 80 so that the plunger 72 is at its depleted lower position, the ratcheting teeth 86 are then positioned adjacent the spherical elements 66 of the reservoir unit 56, the protrusion 73 of the plunger 72 is then received and locked in the notch defined by the notched ramp 67, and the threaded distal end 70 of the fingers 68 are adjacent the non-threaded portion of the post 88. In this depleted or lowermost orientation, the plunger 72 is fixed and prevented from further rotation or advancement by the notched ramp 63, and the cap unit 80 is free to rotate in either direction because the threaded distal end 70 is free to rotate by the non-threaded section of the post 88 and the ratcheting teeth 86 are free to rotated along the spherical elements 66.

Now that the reservoir unit 56 is depleted of insulin 78, the cap unit 80 can be removed by pulling the cap unit 80 away from the reservoir unit 56 along substantially its longitudinal axis. The cap unit 80 is able to be pulled out because of the angled configuration and the semi-stiff nature of the fingers 68 which bend or flex outwardly by the upward pulling motion of the post 88, thereby disengaging the threaded distal ends 70 from the threaded post 88.

Once the cap unit 80 is removed, the user can then remove the reservoir unit 56 by depressing the top planar surface 34 of the latch 30, 30' against the force of the biasing element 36, 44 so that the angled inner surface 32 of the latch 30, 30' pivot away from the base 58 of the reservoir unit 56. Then the reservoir unit 56 can be pulled away from the base unit 12 and discarded or recycled. When the reservoir unit 56 is removed, the sheath 26 will then extend or pop back out over the proximal end of the needle 16 by the resiliency of the rubber sheath 26.

A new reservoir cap 56 can then be attached to the base unit, and the cap unit 80 can be attached to the reservoir unit 56, or the sheath cap 29 can then be reattached, and the base unit 12 removed from the skin 8 of the patient and discarded or recycled.

It can be appreciated that the wearable, disposable insulin reservoir and administration device of the present invention can be modified so as to be used with existing insulin pump insertion sites, such as but not limited to, the Cleo® 90 Infusion Set, Accu-Check Ultraflex™ Set, Medtronic Paradigm Silhouette™, Medtronic Quickset, and Unomedical™ Comfort Set. Where an alternate embodiment base unit can be used as an adaptor to connect the reservoir unit to the infusion set.

While a preferred embodiment of the wearable, disposable insulin reservoir and administration device has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Although delivering a dosage of insulin or medicament to a user discreetly and efficiently have been described, it should be appreciated that the wearable, disposable insulin reservoir and administration device herein described is also suitable for delivering any liquid to a location in metered dosages.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A fluid reservoir and administration device for delivering a dosage of a medicament to a patient, said device comprising:
   a base unit having a main support, at least one latching member, and at least one needle extending through said main support;
   a reservoir unit having a housing defining a cavity therein filled with a fluid, at least one ratcheting element located on said housing, a threaded member, and a plunger moveable received in said cavity, said housing further including a base configured to be releasably secured to said main support of said base unit by said latching member of said base unit; and
   a cap unit having a side wall, a top wall, a defined open bottom configured to receive said reservoir unit therein, a plurality of ratcheting teeth engagable with said ratcheting element of said reservoir unit, and a threaded post threadably engagable with said threaded member of said reservoir unit, said threaded post having a distal end configured to be contact with and move said plunger of said reservoir unit when said cap unit is rotated;
   wherein said proximal end of said needle of said base unit being in fluid communication with said fluid in said cavity of said reservoir unit when said reservoir unit is fitted to said base unit;
   wherein said reservoir unit further comprising at least one ramp adjacent said side wall and said main support, said ramp defining a notch configured to receive a protrusion extending from said plunger of said reservoir unit when said plunger is adjacent said main support.

2. The fluid reservoir and administration device according to claim 1, wherein said ratcheting element of said reservoir unit being located on an exterior of said housing, said ratcheting teeth of said cap unit extending interiorly from said side wall of said cap unit, and said threaded post of said cap unit extending interiorly from said top wall toward said open bottom.

3. The fluid reservoir and administration device according to claim 1, wherein said main support of said base unit further comprising an adhesive layer.

4. The fluid reservoir and administration device according to claim 1, wherein main support of said base unit further comprising at least one ridge located adjacent a periphery of said main support, said ridge being configured to guide and retain said base of said reservoir unit in a position on said base unit.

5. The fluid reservoir and administration device according to claim 1, wherein said base unit further comprising a sheath fixed to said main support and positioned so as to cover a proximal end of said needle.

6. The fluid reservoir and administration device according to claim 5, wherein said sheath having at least a side, and an occluding portion that has a thickness greater than said side, said sheath is flexible allowing said proximal end of said needle to perforate said occluding portion of said sheath when said sheath is depressed.

7. The fluid reservoir and administration device according to claim 1, wherein said reservoir unit further comprising a spherical element between a distal end of said ratcheting element and said base, said spherical element being configured to engage with said ratcheting teeth of said cap unit in multiple rotational directions when said ratcheting teeth are adjacent said spherical element respectively.

8. The fluid reservoir and administration device according to claim 1, wherein said base of said reservoir unit further comprising a seal configured to be perforated by said proximal end of said needle when said reservoir unit is fitted to said base unit.

9. The fluid reservoir and administration device according to claim 1, wherein said threaded member of said reservoir unit being multiple fingers extending angularly away from said top wall of said reservoir unit and toward each other, each of said fingers having a distal end which terminates before contacted said distal ends of the remaining said fingers and which face each other, said distal ends including threads so as to define a threaded opening between the distal ends of said fingers.

10. The fluid reservoir and administration device according to claim 1, wherein said threaded post of said cap unit having a non-threaded portion adjacent said top wall of said cap unit, said non-threaded portion being configured to allow said cap unit to freely rotate in multiple rotational directions when said ratcheting teeth of said cap unit are adjacent spherical elements located between said ratcheting member and said main support of said reservoir unit.

11. The fluid reservoir and administration device according to claim 1, wherein said fluid in said cavity of said reservoir unit is insulin.

12. A medicament reservoir and administration device comprising:
   a base unit having a main support, at least one latching member, at least one needle extending through said main support, an adhesive layer, and a sheath configured to cover a proximal end of said needle;
   a reservoir unit having a housing defining a cavity therein filled with a fluid, at least one ratcheting element located on an exterior of said housing, a threaded member, and a plunger moveable received in said cavity, said housing further including a base configured to be releasable secured to said main support of said base unit by said latching member of said base unit; and
   a cap unit having a side wall, a top wall, a defined open bottom, a plurality of ratcheting teeth extending interiorly from said side wall adjacent said open bottom, and a threaded post extending interiorly from said top wall toward said open bottom, said ratcheting teeth being configured to engage with said ratcheting member of said reservoir unit respectively, said threaded post being configured to threadably engage with said threaded member of said reservoir unit, said threaded post having a distal end configured to be contact with and move said plunger of said reservoir unit when said cap unit is rotated;

wherein said proximal end of said needle of said base unit being in fluid communication with said fluid in said cavity of said reservoir unit when said reservoir unit is fitted to said base unit;

wherein said cap unit is able to freely rotate in multiple rotational directions when said cap unit is adjacent said base of said reservoir unit.

13. The fluid reservoir and administration device according to claim 12, wherein said sheath having at least a side, and an occluding portion that has a thickness greater than said side, said sheath is flexible allowing said proximal end of said needle to perforate said occluding portion of said sheath when said sheath is depressed.

14. The fluid reservoir and administration device according to claim 12, wherein said reservoir unit further comprising a spherical element between a distal end of said ratcheting element and said base, said spherical element being configured to engage with said ratcheting teeth of said cap unit in multiple rotational directions when said ratcheting teeth are adjacent said spherical element respectively.

15. The fluid reservoir and administration device according to claim 12, wherein said base of said reservoir unit further comprising a seal configured to be perforated by said proximal end of said needle when said reservoir unit is fitted to said base unit.

16. The fluid reservoir and administration device according to claim 12, wherein said threaded member of said reservoir unit being multiple fingers extending angularly away from said top wall of said reservoir unit and toward each other, each of said fingers having a distal end which terminates before contacted said distal ends of the remaining said fingers and which face each other, said distal ends including threads so as to define an threaded opening between the distal ends of said fingers.

17. The fluid reservoir and administration device according to claim 12, wherein said reservoir unit further comprising at least one ramp adjacent said side wall and said main support, said ramp defining a notch configured to receive a protrusion extending from said plunger of said reservoir unit when said plunger is adjacent said main support.

18. The fluid reservoir and administration device according to claim 12, wherein said threaded post of said cap unit having a non-threaded portion adjacent said top wall of said cap unit, said non-threaded portion being configured to allow said cap unit to freely rotate in multiple rotational directions when cap unit is adjacent said base of said reservoir unit.

19. The fluid reservoir and administration device according to claim 12, wherein said fluid in said cavity of said reservoir unit is insulin.

* * * * *